United States Patent
Jacobson et al.

(10) Patent No.: US 9,642,845 B2
(45) Date of Patent: May 9, 2017

(54) METHOD FOR ALLEVIATING SIDE EFFECTS OF RETINOIC ACID THERAPY AND/OR IMPROVING EFFICACY WITHOUT INTERFERING WITH EFFICACY

(75) Inventors: Elaine L. Jacobson, Tucson, AZ (US);
Myron K. Jacobson, Tucson, AZ (US);
Russell Coyle, Tucson, AZ (US);
Hyuntae Kim, Tucson, AZ (US);
Donna L. Coyle, Tucson, AZ (US)

(73) Assignee: University of Kentucky Research Foundation, Lexington, KY (US)

( * ) Notice: Subject to any disclaimer, the term of this patent is extended or adjusted under 35 U.S.C. 154(b) by 1400 days.

(21) Appl. No.: 12/449,793

(22) PCT Filed: Feb. 27, 2008

(86) PCT No.: PCT/US2008/002605
§ 371 (c)(1),
(2), (4) Date: Mar. 23, 2010

(87) PCT Pub. No.: WO2008/106177
PCT Pub. Date: Sep. 4, 2008

(65) Prior Publication Data
US 2010/0173957 A1  Jul. 8, 2010

Related U.S. Application Data

(60) Provisional application No. 60/903,937, filed on Feb. 28, 2007.

(51) Int. Cl.
*A01N 43/40* (2006.01)
*A61K 31/435* (2006.01)
*A61K 31/455* (2006.01)
*A61K 8/67* (2006.01)
*A61K 31/203* (2006.01)
*A61Q 19/00* (2006.01)

(52) U.S. Cl.
CPC ............ *A61K 31/455* (2013.01); *A61K 8/671* (2013.01); *A61K 8/675* (2013.01); *A61K 31/203* (2013.01); *A61Q 19/00* (2013.01); *A61K 2800/75* (2013.01); *A61K 2800/88* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 6,677,361 B2 * | 1/2004 | Jacobson et al. | 514/356 |
| 2001/0033848 A1 * | 10/2001 | Jacobson et al. | 424/401 |
| 2002/0137693 A1 * | 9/2002 | Kang et al. | 514/27 |
| 2007/0009474 A1 * | 1/2007 | Xie et al. | 424/74 |

OTHER PUBLICATIONS

Catz et al. "Simultaneous determination of myristyl nicotinate, nicotinic acid, and nicotinamide in rabbit plasma by liquid chromatography-tandem mass spectrometry using methyl ethyl ketone as a deproteinization solvent", J. Chromatography B, 2005, vol. 829, pp. 123-135.*
Chemical Abstracts Service Registry No. 98-92-0, "Niacinamide" (Accessed May 28, 2012).*
Chemical Abstracts Service Registry No. 302-79-4, "Tretinoin" (Accessed May 28, 2012).*
National Institutes of Health, National Library of Medicine Medical Subject Headings (MeSH) index term "Nicotinic Acids" (Accessed Jun. 1, 2012).*
Chemical Abstracts Service Registry No. 273203-62-6, "myristyl nicotinate" (Accessed Sep. 23, 2014).*
Draelos, et al., "Facilitating Facial retinization Through Barrier Improvement," Cutis., 78:275-281 (2006).
Tashtoush, et al., "Analysis and stability study of myristyl nicotinate in dermatological preparations by high-performance liquid chromatography," Journal of Pharmaceutical and Biomedical Analysis, 43:893-899 (2007).

* cited by examiner

*Primary Examiner* — Jeffrey S Lundgren
*Assistant Examiner* — Stephanie Springer
(74) *Attorney, Agent, or Firm* — Abelman, Frayne & Schwab

(57) ABSTRACT

The invention relates to the use of nicotinic acid alkyl esters, especially myristyl nicotinate, to inhibit side effects associated with retinoic acid therapy. Also a part of the invention is a method for improving skin cell differentiation by administering the nicotinic acid alkyl ester in an amount sufficient to increase expression of caspase 14 and filaggrin. Deficiencies in expression of these molecules can be treated in this way as well.

7 Claims, No Drawings

METHOD FOR ALLEVIATING SIDE EFFECTS OF RETINOIC ACID THERAPY AND/OR IMPROVING EFFICACY WITHOUT INTERFERING WITH EFFICACY

RELATED APPLICATION

This application is a 371 application from PCT/US2008/002605 filed Feb. 27, 2008, which claims priority of Provisional application Ser. No. 60/903,937 filed Feb. 28, 2007, and incorporated by reference in their entirety.

FIELD OF THE INVENTION

The invention relates to the use of niacin derivatives to alleviate side effects resulting from retinoic acid therapy and/or improving efficacy without interfering with efficacy of retinoic acid therapy. More particularly, niacin derivatives, such as straight chain nicotinic acid alkyl esters, myristyl nicotinate in particular, alleviate side effects from retinoic acid therapy such as, but not exclusively, tightness/dryness, stinging, burning, and tingling, as discussed infra. Also a feature of the invention is the improvement of skin cell differentiation by increasing expression of caspase-14 and filaggrin.

BACKGROUND OF THE INVENTION

Retinoids, the natural metabolites and synthetic analogues of vitamin A (retinol), are important regulators of skin function. Fisher, et al., *Faseb J* 1996; 10: 1002-13. All-trans-retinoic acid (vitamin A acid), the major naturally occurring biologically active retinoid, has been a focus of research for possible use in topical treatments for photodamaged skin, for many years. In 1986, it was reported that retinoic acid could produce smoother, less wrinkled, and less pigmented skin after a few months of treatment. Kligman et al., *J Am Acad Dermatol* 1986; 15: 836-59.

Long-term exposure of skin to sunlight leads to a series of progressive changes that range from loss of skin texture and tone to thinning of the epidermis and stratum corneum (Gilchrest, *Br J Dermatol* 1996; 135: 867-75), flattening of the dermal-epidermal junction (Benedetto, *Clin Dermatol* 1998; 16: 129-39), generation of areas of hyperpigmentation (Gilchrest, supra), wrinkles, and accumulation of keratinocytes with atypical morphology that are likely precursors to actinic keratoses and non melanoma skin cancers (Cho, et al., *J Am Acad Dermatol* 2005; 53: 769-74; Lober, et al., *J Am Acad Dermatol* 2000; 43: 881-2). Photodamage occurs in both the epidermal and dermal compartments, where retinoids have been shown to have prominent pharmacological effects. Gendimenico, et al., *Skin Pharmacol* 1993; 6 Suppl 1: 24-34; Varani, et al., *J Invest Dermatol* 2000; 114: 480-6; Cho, et al., supra. In the epidermis of photodamaged skin, long-term topical retinoid therapy results in dose dependent increases in epidermal and granular layer thickness, stratum corneum compaction, decreased melanin content and improvement of epidermal atypia. Fisher et al., supra; Cho, et al., supra; Olsen, et al., *J Am Acad Dermatol* 1992; 26: 215-24; Machtinger, et al., *Br J Dermatol* 2004; 151: 1245-52. In keratinocytes, retinoids induce proliferation, presumably mediated by epidermal growth factor receptor activation resulting in epidermal hyperplasia. Rittie, et al., *J Invest Dermatol* 2006; 126: 732-9.

Retinoic acid induced expression of keratins K6, K16, and K17, which are commonly expressed in hyperproliferative epidermal cells, indicates that retinoids increase cell proliferation in the basal and/or lower spinous layers of the epidermis. Eichner, et al., *Br J Dermatol* 1996; 135: 687-95. Retinoids also can lighten hyperpigmented skin, reduce tyrosinase activity in cultured melanocytic cells (Hoal, et al., *Cancer Res* 1982; 42: 5191-5; Kang, et al., *Am J Clin Dermatol* 2005; 6: 245-53), inhibit proliferation and lipid synthesis, and alter keratin expression in cultured human sebocytes. Zouboulis, et al., *J Invest Dermatol* 1991; 96: 792-7. In the dermis, effects include increased fibroblast proliferation (Varani, et al., supra), increased collagen production (Griffiths, et al., *N Engl J Med* 1993; 329: 530-5), and reduced extracellular matrix degradation (Fisher and Voorhees, supra).

The degradation of collagen in the dermis is a major factor in the formation of skin wrinkles. Prolonged use of retinoic acid significantly increases collagen matrix deposition in dermal repair zones and this effect appears to be responsible for the wrinkle reduction that accompanies retinoic acid treatment of photodamaged skin. (Cho, et al., supra; Kang, et al., supra).

While retinoic acid provides multiple benefits to photodamaged skin (Kang, et al., supra), it is frequently accompanied by significant skin irritation that limits compliance with therapy. Lowe, et al., *J Cosmet Laser Ther* 2004; 6: 79-85. The most commonly reported retinoic acid treatment-related adverse effects are irritation, dryness, peeling, erythema, and a sensation of burning on the skin. Lowe, et al., supra. These side effects often result in discontinuation of therapy.

Hence, a method to diminish or eliminate the side effects associated with retinoic acid therapy is needed.

The mechanisms that lead to retinoid side effects are still incompletely understood but retinoic acid therapy is known to impair stratum corneum barrier function as assessed by TEWL measurements. Tagami, et al., *Br J Dermatol* 1992; 127: 470-5. Barrier impairment has been attributed to retinoid-induced epidermal hyperplasia (Varani, et al., *Arch Dermatol Res* 2003; 295: 255-62) and to alteration of the terminal differentiation program (Fisher, et al., supra). Erythema, which reflects the production of epidermal cytokines such as IL-1, may result from retinoid-stimulated keratinocyte proliferation directly or as a consequence of epidermal barrier impairment. Wood, et al., *J Invest Dermatol* 1996; 106: 397-403; Blanton, et al., *Proc Natl Acad Sci USA* 1989; 86: 1273-7. Retinoid-induced stratum corneum compaction (Olsen, et al., supra; Machtinger, et al., supra) is likely related to barrier impairment as stratum corneum thickness is a major determinant of barrier function (Ya-Xian, et al., *Arch Dermatol Res* 1999; 291: 555-9; de Jongh, et al., *Br J Dermatol* 2006; 154: 651-7).

Niacin derivatives have been developed for optimal topical delivery of nicotinic acid to skin (Jacobson, et al., Developing Topical Prodrugs for Skin Cancer Prevention. In: *Fundamentals of Cancer Prevention* (Alberts D S, Hess, Lisa M., ed). Berlin Heidelberg: Springer-Verlag, 2005: 139-60) and have been shown to enhance epidermal differentiation in photodamaged skin, resulting in increased stratum corneum and epidermal thickness and enhanced skin barrier function as assessed by decreased rates of TEWL. Jacobson, et al., Experimental Dermatology, in press. Niacin derivatives are also described in U.S. Pat. Nos. 6,337,065, 6,677,361, 6,750,234 and 6,924,299, each of which is incorporated by reference in its entirety.

One such niacin derivative is myristyl nicotinate, which was developed for optimal topical delivery of nicotinic acid to skin. Myristyl nicotinate has been shown to enhance epidermal differentiation in photodamaged skin, resulting in increased stratum corneum and epidermal thickness and enhanced skin barrier function as assessed by decreased rates of TEWL. Jacobson, et al., *Experimental Dermatology*, in press.

Hence, it is an object of the present invention to treat the side effects caused by retinoic acid therapy with niacin derivatives. A further feature of the invention is the improvement of skin cell differentiation via use of these niacin derivatives.

DETAILED DESCRIPTION OF PREFERRED EMBODIMENTS

EXAMPLE 1

A clinical study was conducted to examined the combined use of retinoic acid therapy with myristyl nicotinate (MN), a lipophilic derivative of niacin that enhances skin barrier function, in subjects with mild to moderate facial photodamage.

All subjects selected for the study were female, between the ages of 30 and 60, with a score of I to IV on the Fitzpatrick Skin Classification, mild to moderate photodamaged skin as defined by a modified Glogau Classification of I to II, and with presence of dyschromia on the face as determined by a woods light visual scan.

The subjects were randomly assigned to one of three groups of 20 subjects each. One month prior to the initiation of retinoic acid therapy, one of the groups (group 3) began to apply to the entire face, both night and morning, a formulation containing 5% myristyl nicotinate. Groups 1 and 2 applied, in the same manner, a placebo formulation in which myristyl myristate replaced myristyl nicotinate. Upon initiation of retinoic acid therapy (baseline), group 1 (placebo/placebo+RA) continued to use the placebo formulation as above, group 2 (placebo/MN+RA) initiated use of the 5% myristyl nicotinate formulation and group 3 (MN/MN+RA) continued to use the 5% myristyl nicotinate formulation. Retinoic acid therapy involved a 0.025% concentration of the drug applied at night, immediately following application of the placebo or myristyl nicotinate containing formulations. This strength of retinoic acid was chosen for this study as the subjects had mild to moderate photodamage.

Subjects also were provided with mild liquid cleansers and sunscreen to use for facial cleansing and sun protection during the entire course of the study. Subjects applied the assigned test moisturizers [myristyl nicotinate (5%) or a placebo that contained myristyl myristrate replacing myristyl nicotinate] to their entire face twice per day after cleansing. During the usage phase of the study, subjects applied the retinoic acid formulation (0.025%) to their face after test moisturizer application once per day in the evening.

The effects of the 5% myristyl nicotinate formulation on surrogate markers of skin barrier function, clinical and sensory irritation, and clinical efficacy associated with retinoic acid use were evaluated. Periorbital skin biopsy samples were evaluated for stratum corneum thickness and rates of transepidermal water loss (TEWL) were determined as surrogate measures of barrier function, tolerability was evaluated by clinical grading, and efficacy was assessed by clinical grading, patient self-assessment, and analysis of biopsy samples for epidermal thickness.

Stratum corneum compaction typically accompanies retinoic acid therapy and studies relating increased barrier function to an increased stratum corneum thickness (Ya-Xian, et al., supra; de Jongh, et al., supra) raise the possibility that stratum corneum compaction is one factor involved in the barrier impairment associated with retinoic acid therapy.

Accordingly, periorbital biopsy samples obtained from study subjects were evaluated for stratum corneum thickness. A board certified dermatologist collected a 2-mm punch biopsy from the right or left side of the face as determined by a randomization design of 7 randomly selected subjects from each group at baseline and after 12 weeks of treatment. The punch biopsies were formalin-fixed, embedded in paraffin, cut into 5 µm cross-sections, mounted on slides, and stained with hematoxylin-eosin (H&E).

Histological images were taken of the H&E stained cross sections with an Olympus inverted stage microscope using a 10× by 0.45 Apochromat objective and a Nikon digital CCD camera. ImageJ image analysis software (NIH) was used to examine the images and perform measurements. Suprapapillary epidermal thickness (as measured from the top of the dermal papilla to the top of the granular layer) and stratum corneum thickness (as measured from the top of the granular layer to the top of the stratum corneum) were measured. For each specimen, five different sites were measured and the average was calculated.

At baseline, the mean stratum corneum thickness value of the placebo/MN+RA group was slightly higher than the placebo/placebo+RA group, although the difference was not statistically significant. The mean stratum corneum thickness of the MN/MN+RA group, which had been treated for one month with 5% myristyl nicotinate, was higher than the other two groups, although the difference did not reach statistical significance at $p<0.05$. However, previous studies have shown that treatment of photodamaged skin with 5% myristyl nicotinate for 3 months results in an increase in stratum corneum thickness of more than 50%. Thus the approximately 11% higher mean value of MN/MN+RA group compared to the mean values of the other groups agrees with the known effect of myristyl nicotinate.

During the 12 weeks of retinoic acid therapy, the placebo/placebo+RA group experienced a reduction in stratum corneum thickness of approximately 24% ($p=0.006$ vs. baseline), while concurrent use of myristyl nicotinate and retinoic acid did not result in a decrease in stratum corneum thickness. The difference in mean stratum corneum thickness between the placebo/placebo+RA and placebo/MN+RA group at 12 weeks of therapy was highly statistically significant ($p=0.005$). The difference between the MN/MN+RA group and the placebo/placebo+RA group at 12 weeks also was highly statistically significant ($p=0.003$). These results show that concurrent or prior and concurrent use of myristyl nicotinate mitigates stratum corneum compaction associated with retinoic acid therapy.

Determination of rates of TEWL provides a non-invasive assessment of relative skin barrier function. Hence, TEWL measurements were taken from the faces of study subjects and used as a surrogate marker of barrier function to compare placebo and myristyl nicotinate treated groups. For the TEWL measurements, the instruments required a specified temperature and humidity range for optimal function, thus subjects were required to equilibrate to ambient conditions for at least 20 min prior to measurements. Temperature was maintained between 66 and 72° F. and relative humidity maintained between 15 and 55%. A computer-linked Dermalab instrument was used to measure TEWL at two points above the skin surface on the right cheeks of study subjects and the rate of water loss was calculated. Each TEWL measurement was averaged over a one-min measurement period.

The rates of TEWL increased in the placebo/placebo+RA group by during the 12 week period approximately 45%, a value that was highly statistically significant (p<0.0001). The mean rates of TEWL also increased in the placebo/MN+RA and MN/MN+RA groups, although the changes from baseline for these groups were not statistically significant. The difference between the placebo/placebo+RA and MN/MN+RA groups at 12 weeks (p=0.056) demonstrated a strong trend towards statistical significance.

These results indicate that concurrent use of myristyl nicotinate mitigates barrier impairment and that prior use plus concurrent use provides greater barrier protection than concurrent use alone.

Clinical Grading

In order to assess both the tolerability and efficacy of retinoic acid therapy, subjects also were clinically graded on the right and/or left side of the face for efficacy/performance parameters and irritation/safety parameters at baseline, and weeks 2, 4, 8, and 12.

The most severe parameters of tolerability such as scaling/peeling and degree of erythema were graded on 3-point clinical scale at weeks 2, 4, 8, and 12, and mean values were determined. The frequency of less severe parameters of tolerability typical of retinoic acid therapy (including tightness/dryness, stinging, burning, and tingling) was also evaluated.

The degree of scaling/peeling was very low in all groups and the degree of erythema also was relatively low, indicating an overall high degree of tolerance of the 0.025% concentration of retinoic acid and/or the regular use of a moisturizer twice per day prior to and during therapy. There were no statistically significant differences between placebo and myristyl nicotinate groups in either parameter, although the grading of erythema was consistently slightly higher in the myristyl nicotinate treated subjects.

Despite the low levels of scaling/peeling or erythema, a significant frequency of less severe but commonly encountered side effects of retinoic acid were observed in the study. For these tolerability parameters, a consistent pattern was observed as concurrent use of myristyl nicotinate decreased the frequency of tightness/dryness, stinging, and burning, and prior and concurrent myristyl nicotinate use further reduced the frequency of each of these parameters. Although the frequency of tingling reported was quite low (2%), the incidence of this side effect was reduced to zero for the MN/MN+RA group.

In addition to the clinical grading, study subjects completed self-assessment questionnaires that solicited information related to tolerability of the therapy. These self-assessments paralleled the clinical grading in all cases where the same parameter was assessed. In total, the results show that use of myristyl nicotinate improved the tolerability of retinoic acid therapy.

Expert clinical grading, patient self-assessment, and analysis of biopsy samples for epidermal thickness were also used to examine the effect of myristyl nicotinate on the efficacy of retinoic acid therapy.

Clinical grading involved evaluation of dyschromia, fine lines, shallow wrinkles, tactile roughness, and temple laxity as a function of treatment time (at weeks 2, 4, 8, and 12). Despite some differences in the degree of initial photodamage between the groups, similar rates of improvement for all three groups were observed for dyschromia, fine lines, and shallow wrinkles. This also was observed for tactile roughness although scores for the MN/MN+RA group consistently showed greater improvement from weeks 4 to 12. Grading of temple laxity showed a statistically significant greater improvement (p=0.02) at 12 weeks in the MN/MN+RA group compared to the placebo/placebo+RA and a trend for greater improvement for the placebo/MN+RA compared to placebo/placebo+RA was observed that did not reach statistical significance at p<0.05.

Study subjects also completed a self-assessment questionnaire at the completion of the study that related to their assessment of efficacy. This questionnaire requested study subjects to respond to questions with one of 5 choices (Strongly agree, agree, neither agree nor disagree, disagree, strongly disagree). In no case did subjects in the groups using myristyl nicotinate rate efficacy lower than subjects in the placebo/placebo+RA group and in four of the five questions a greater percentage of study subjects using myristyl nicotinate perceived improved efficacy compared to the placebo group. These results indicate that concurrent or prior and concurrent use of myristyl nicotinate did not interfere with retinoic acid efficacy and by some parameters resulted in improved efficacy.

Since long term retinoid therapy is associated with an increase in epidermal thickness, changes in epidermal thickness in each of the groups over the 12-week course of the retinoic acid therapy were also assessed. The mean values for the placebo/placebo+RA, placebo/MN+RA, and MN/MN+RA groups at the baseline were 37.9, 38.8, and 39.3 µm, respectively. The mean epidermal thickness of the group receiving retinoic acid and the placebo cream decreased by approximately 5% over the 12 week study. The epidermal thickness of the group concurrently receiving myristyl nicotinate increased by approximately 3% and the group receiving myristyl nicotinate prior/concurrent with retinoic acid increased by approximately 10%. The difference between the placebo/placebo+RA and MN/MN+RA groups at 12 weeks was statistically significant (p=0.0007) while the difference between placebo/placebo and placebo/MN+RA groups showed a trend but did not reach statistical significance at p<0.05. The difference between the placebo/MN+RA and MN/MN+RA groups at 12 weeks also reached statistical significance (p=0.05).

The results of clinical grading, self-assessment and epidermal thickness determinations indicate that the efficacy of retinoic acid therapy was not negatively affected by myristyl nicotinate. Further, the results indicate that the use of myristyl nicotinate increased efficacy of retinoic acid therapy.

EXAMPLE 2

Caspase-14 has been shown to be a unique protease which controls maturation of the epidermis. This control results from proteolytic processing of filaggrin, a protein that is recognized as being involved in late stages of skin cell differentiation. The products of the action of caspase-14 on filaggrin prevent UVB photodamage, as well as water loss. See, e.g., Nicotera, et al., *Nature Cell Biology* 9:621-622 (2007); Denecker, et al., *Nature Cell Biology* 9:666-674 (2007), both of which are incorporated by reference.

Rendl, et al., *J. Investigative Dermatol* 119:1150-1155 (2002), incorporated by reference, have shown that retinoids down regulate caspase 14.

The interrelationships amongst caspase 14, filaggrin, and retinoids suggested that they might be impacted by myristyl nicotinate.

To investigate this, the levels of expression of both caspase 14 and filaggrin were investigated in the groups of subjects referred to supra, (i.e., subjects who received placebo alone for one month, then placebo plus retinoic acid, and those who received placebo only for one month and then myristyl nicotinate and retinoic acid during the treatment phase.

An average increase of 5% in caspase 14 expression was found in subjects who received placebo plus retinoic acid for 3 months, while subjects who received placebo, retinoic acid and myristyl nicotinate for 3 months showed a 24% increase in caspase 14 expression over the same period.

With respect to filaggrin expression, subjects receiving placebo, myristyl nicotinate and retinoic acid showed an average increase of 13%, while subjects not treated with myristyl nicotinate showed no change.

These results clearly establish a link between myristyl nicotinate and the beneficial effects of the interplay of caspase 14 and filaggrin, on skin cell differentiation, as discussed supra.

The foregoing description sets forth various features of the invention which include, inter alia, a method for alleviating a side effect of retinoic acid therapy and/or improving efficacy and/or not interfering with efficacy in a patient receiving said therapy, by administering an amount of a nicotinic acid derivative, such as a nicotinic acid ester. Preferably, this is a nicotinic acid alkyl ester. Especially preferred are nicotinic acid alkyl esters, where the ester moiety contains from 10-18 carbon atoms.

The mode by which the nicotinic acid ester is administered to the subject may vary. Oral, time release, intravenous, intradermal, and other forms of administration are contemplated, as is topical administration.

Topical administration refers to the application of a nicotinic acid ester to the external surface of the skin or the mucous membranes (including the surface membranes of the nose, lungs and mouth), such that the nicotinic acid ester crosses the external surface of the skin or mucous membrane and enters the underlying tissues. In the preferred form, the nicotinic acid ester is applied topically for dermal or transdermal delivery of nicotinic acid. Transdermal delivery refers to the diffusion of a nicotinic acid ester across the barrier of the skin after which it is bioconverted to nicotinic acid by skin esterases. Absorption through intact skin can be enhanced by placing the nicotinic acid ester in an oily vehicle before application to the skin (a process known as inunction). Passive topical administration may consist of applying the nicotinic acid ester directly to the treatment site in combination with emollients or penetration enhancers.

Such topical administration is particularly preferred and may be via a cream, lotion, liquid, aerosol, body wash, mouthwash, toothpaste, gavage, or other form of topical administration. For example, in the case of timed released application, "patches," such as the type used in timed release of nicotine, bandages, wraps, and so forth may be employed.

The nicotinic acid ester is administered in an amount sufficient to alleviate a side effect of retinoic acid therapy. The dose used can and will vary.

Another feature of the invention is the a method for improving mature skin cell differentiation, by administering an amount of a nicotinic acid alkyl ester, as described supra, in an amount sufficient to increase expression of caspase 14 and filaggrin. Increased expression of these two molecules lead to increased interactions, which in turn leads to improvements in skin cell differentiation. Myristyl nicotinate is especially preferred.

Other aspects of the invention will be clear to the skilled artisan and need not be set forth herein. The terms and expressions which have been employed are used as terms of description and not of limitation, and there is no intention in the use of such terms and expressions of excluding any equivalents of the features shown and described or portions thereof, it being recognized that various modifications are possible within the scope of the invention.

The invention claimed is:

1. A method for alleviating or preventing a side effect caused by retinoic acid without interfering with efficacy of said retinoic acid, comprising administering an amount of a nicotinic acid alkyl ester selected from the group consisting of myristyl nicotinate and palmityl nicotinate sufficient to alleviate or to prevent said side effect, to a subject for at least one month prior to said subject receiving, or while said subject is receiving, said retinoic acid.

2. The method of claim 1 wherein said nicotinic acid alkyl ester is administered topically.

3. The method of claim 1, wherein said nicotinic acid alkyl ester is administered by dermal or transdermal delivery.

4. The method of claim 1, comprising administering said nicotinic acid alkyl ester concurrently with said retinoic acid.

5. The method of claim 1, further comprising administering said nicotinic acid alkyl ester to said subject for at least one month prior to administration of said retinoic acid.

6. The method of claim 1, wherein said subject is a mammal.

7. The method of claim 6 wherein said mammal is a human.

* * * * *